(12) United States Patent
Grant et al.

(10) Patent No.: US 7,022,992 B2
(45) Date of Patent: Apr. 4, 2006

(54) METHOD AND APPARATUS FOR REAL-TIME MONITORING OF FURNACE FLUE GASES

(75) Inventors: Michael Grant, Chicago, IL (US); Ovidiu Marin, Lisle, IL (US); Erwin Penfornis, Oak Park, IL (US); William A. Von Drasek, Oak Forest, IL (US)

(73) Assignee: American Air Liquide, Inc., Fremont, CA (US)

( * ) Notice: Subject to any disclaimer, the term of this patent is extended or adjusted under 35 U.S.C. 154(b) by 255 days.

(21) Appl. No.: 10/314,916

(22) Filed: Dec. 9, 2002

(65) Prior Publication Data
US 2003/0160174 A1    Aug. 28, 2003

Related U.S. Application Data (60) Provisional application No. 60/349,867, filed on Jan. 17, 2002.

(51) Int. Cl.
*G01J 5/02* (2006.01)

(52) U.S. Cl. .......................... 250/339.13; 250/339.06; 250/339.01; 250/338.1; 250/336.1

(58) Field of Classification Search ........... 250/339.12, 250/339.06, 339.01, 338.1, 336.1, 339.13
See application file for complete search history.

(56) References Cited

U.S. PATENT DOCUMENTS

| | | | |
|---|---|---|---|
| 4,514,780 A * | 4/1985 | Brussee et al. | 361/226 |
| 4,627,269 A * | 12/1986 | Forster et al. | 73/31.06 |
| 4,928,015 A * | 5/1990 | Butler et al. | 250/343 |
| 4,990,780 A | 2/1991 | Lee et al. | |
| 5,026,992 A * | 6/1991 | Wong | 250/343 |
| 5,070,246 A | 12/1991 | Durham et al. | |
| 5,173,749 A * | 12/1992 | Tell et al. | 356/437 |
| 5,550,636 A | 8/1996 | Hagans et al. | |
| 5,984,998 A | 11/1999 | Ottesen et al. | |
| 6,061,141 A * | 5/2000 | Goldenberg et al. | 356/437 |
| 6,064,488 A | 5/2000 | Brand et al. | |

FOREIGN PATENT DOCUMENTS

DE    19724863 A1    12/1998

OTHER PUBLICATIONS

PCT Search Report for PCT/IB 0300050.

Ellis R.S., et al.: "Installation and Operation of a Reliable High Temperature Oxygen Analysis For FCCU Flue Gas Monitoring" Advances in Instrumentation and Control, Instrument Society of America, Research Triangle Park, US vol. 49, No. Part 3, Oct. 23, 1994, pp. 1049-1053, XP000509012 ISSN:1054-0032 figure 1.

Licki J., et al: "Off-Line System For Measurement of Nitrous Oxide Concentration in Gases Leaving the Irradiation Chamber" Radiation Physics and Chemistry, Elsevier Science Publishers BV., Amsterdam, NL, vol. 45, No. 6, Jun. 1, 1995 pp. 1035-1038, XP004051480, ISSN:0969-806X figure 1.

* cited by examiner

*Primary Examiner*—Otilia Gabor
*Assistant Examiner*—Christine Sung
(74) *Attorney, Agent, or Firm*—Christopher J. Cronin (57) ABSTRACT

A method and apparatus for monitoring the flue gases of a furnace combustion process is disclosed. A by-pass circuit that communicates a sample of flue gases to be monitored from a furnace, through a measurement chamber and back to the furnace or furnace exhaust duct is provided. The by-pass circuit has a gas sampling probe with a fume inlet opening, the probe being positioned for withdrawing the sample to be monitored and transmitting it through the by-pass circuit. A measurement device is positioned in the measurement chamber and comprises an in situ optical device which provides real-time measurement of targeted flue gas species concentrations.

36 Claims, 3 Drawing Sheets

METHOD AND APPARATUS FOR REAL-TIME MONITORING OF FURNACE FLUE GASES

CROSS REFERENCE TO RELATED APPLICATION

This application claims the benefit of U.S. Provisional Application No. 60/349,867, filed Jan. 17, 2002.

BACKGROUND OF THE INVENTION

1. Field of the Invention

This invention relates to a method and apparatus for monitoring the flue gases of an industrial combustion process. A method and an apparatus for sampling and continuously monitoring flue gases from an industrial furnace is disclosed. The method is particularly adapted to processes with hostile environments, characterized by high particulate levels and high temperatures and/or vibrations, such as electric arc furnaces (EAF). The method is also adaptable to any industrial combustion processes where flue gas monitoring is desired. Exhaust gases of a furnace are sampled through an extractive probe and analyzed through a remote optical device, preferably a diode laser, for measurement of flue gas species concentration. Thus, an extractive sampling system is integrated with a non-intrusive optical measurement technique that is resistant to the problems encountered by prior art flue gas monitoring systems. This facilitates more optimal furnace efficiency, as post-combustion of the CO and/or $H_2$ byproducts of the production process can be achieved.

2. Description of the Prior Art

In many industrial furnace operations, and in particular in the recycling of scrap steel in electric arc furnaces, large volumes of carbon monoxide (CO), hydrogen ($H_2$) and/or other combustible gases are frequently vented as components of the flue gases from the furnace. These gases contain heating value that can be recovered to improve furnace efficiency and reduce the cost of steel recovery. These combustible gases form a significant proportion of the waste gas leaving the furnace, which also normally contain a large amount of particulate dust and liquid or semi-liquid slag droplets.

Because of the large amounts of energy used in an electric arc furnace, steel mill operators are increasingly looking for ways to use all potential energy during the steel making process. Hence, a variety of schemes exist to further react the CO and $H_2$ with oxygen prior to their exit from the furnace, to form carbon dioxide ($CO_2$) and water vapor ($H_2O$). These post-combustion reactions of CO, $H_2$ and oxygen are highly exothermic, and therefore release heat to the solid scrap, the slag and the melt phases in the furnace, thus allowing to recover part of the heat content of the gases and to save electrical energy.

To burn the combustible gases, oxygen is injected into the furnace. In order to determine the initiation of, duration of and rate of such oxygen flow, it is necessary to continuously analyze the waste gas (by measuring its oxygen or carbon monoxide content, for example) and to use the resulting measurement to open or modulate oxygen admission valves. Because these post-combustion systems operate on a feedback principle and that combustion in EAF is a very dynamic phenomenon, they must respond quickly to any change in the waste gas composition.

Two major methods for gas composition monitoring in harsh, high particle laden industrial combustion processes can be found: 1) extractive sampling techniques coupled with gas analyzing systems and 2) in situ optical measurement techniques.

Conventional extractive sampling methods for gas composition analysis is performed using a temperature resistant water-cooled probe, a water removal system, primary and secondary particle filters, and a suction pump to withdraw the sample from the process. These components are assembled before the analyzers to ensure the sample is cooled and free of water and particulate matter, which could otherwise damage the analyzer equipment. Since many industrial environments are not suitable for sensitive instrumentation, sampling lines from the process to the analyzer can be up to hundreds of feet in length, introducing a delay that can be up to tens of seconds before reaching the analyzer. Then, analyzers exhibit a characteristic response time that will add to the measurement delay.

Additionally, the waste gas at the position from which samples are normally taken entrains a high concentration of dust and other particulate matter. The particulate matter impacts on the probe and tends to agglomerate thereon, as well as in gas lines used to draw the gas sample to the analyzer. This occurs often to the extent that the probe becomes blocked, necessitating replacement and/or cleaning of the probe.

Thus, while conventional sampling apparatus may be effective in obtaining a single gas sample every few hours, heretofore sampling apparatus have proven ineffective in the continuous collection of samples of furnace flue gases, as they become clogged after extended periods of use. Moreover, many of the existing extractive probes have a limited lifetime due to exposure to high temperatures and high particle density streams, as in the case of EAF installation where they are located in the break flange of the flue gas system.

An alternative to this method, which has been developed to overcome the delay time and maintenance issues associated with extractive sampling techniques, is dealing with in situ optical measurements, viz., absorption techniques. This method and the related apparatus have already been documented in U.S. Pat. No. 5,984,998. Since optical measurements are non-intrusive, no gas extraction is required and thus measurements can theoretically be conducted in the harshest environments containing high particle density atmospheres. This reduces the maintenance issues due to probe plugging and corrosion, as well as the associated cost.

Practically, optical systems based on absorption use sources and detectors located at opposite sides of furnaces. A beam of radiation is launched across the process, thus creating an optical line-of-sight through the flue gas exhaust duct.

Moreover, a unique feature of the method is the fast-time response that allows real-time monitoring of the combustion atmosphere. However, experience from field trials conducted using this optical approach allowed identifying several technical issues that must be taken into consideration. First, in addition to molecular absorption along the optical path, the laser beam may be significantly attenuated in its passage through the flue gas due to scattering caused by the very large number of small particles entrained in the gas flow.

In some cases, the attenuation of incident radiation can be so great to extinguish it completely, thus receiving no exiting radiation and voiding the measurement. Measurement quality can also degrade due to mechanical vibration of the beam launch and receiver. Industrial processes with high vibration will steer the beam on and off the detector resulting in signal noise.

In cases where transmission is acceptable but high particle densities are present, baseline quality of the measurement degrades due to temporal effect of the radiation particle interaction. Another form of noise also due to the beam moving on and off the detector is beam steering resulting from the refractive index gradients in high temperature process streams. It is thus clear that, depending on the process environment under consideration, such in situ optical techniques can significantly loose their accuracy, to the extent that it becomes impossible to obtain a reliable measurement.

Hence, no reliable, accurate and real-time method is currently available for monitoring flue gas species concentrations in high-temperature, high-particulate combustion processes (or at least in electric arc furnaces), which has prevented so far the dynamic control of such processes and the optimization of their efficiency.

Thus, a problem associated with methods for sampling and continuously monitoring flue gases from an industrial furnace that precede the present invention is that they provide a slow response time and thereby do not adequately indicate process conditions to enable optimal process control.

A problem associated with in situ optical measuring techniques for flue gases from an industrial furnace that precede the present invention is that they do not provide point measurements, and therefore do not allow sampling the flue gas specifically in the desired locations of the exhaust stream.

Still another problem associated with methods for monitoring the flue gases of an industrial combustion process that precede the present invention is that they do not facilitate optimal use of the potential energy present in the process by-products for heat generation.

Yet another problem associated with methods for monitoring the flue gases of an industrial combustion process that precede the present invention is that they are susceptible to probe plugging and corrosion.

An even further problem associated with methods for monitoring the flue gases of an industrial combustion process that precede the present invention is that they require undue replacement of the monitoring equipment.

Still a further problem associated with methods for monitoring the flue gases of an industrial combustion process that precede the present invention is that they do not provide continuous, near real-time measurements of the species concentration in the waste gases, with acceptable accuracy, so as to facilitate an adapted dynamic monitoring of process characteristics.

Another problem associated with methods for monitoring the flue gases of an industrial combustion process that precede the present invention is that they do not adequately facilitate control of the CO and $H_2$ combustion by-products.

An even further problem associated with methods for monitoring the flue gases of an industrial combustion process that precede the present invention is that they do not facilitate monitoring of most or all species whose concentration can be measured by absorption techniques, e.g., $H_2$, CO, $O_2$, $H_2O$, $CO_2$, $NO_x$ and/or $SO_x$.

Yet another problem associated with methods for monitoring the flue gases of an industrial combustion process that precede the present invention is that they cannot be used in industrial processes that experience high particle densities, temperature gradients, mechanical vibration, rapid variations in temperature and gas composition, and high radiation loads from the process itself.

Still another problem associated with methods for monitoring the flue gases of an industrial combustion process that precede the present invention is that they have a complex electro-mechanical structure, are expensive to construct and difficult to maintain.

In contrast to the foregoing, the present invention provides a method and apparatus for monitoring the flue gases of an industrial combustion process that seeks to overcome the foregoing problems and provide a more simplistic, more easily constructed and relatively reliable methodology.

SUMMARY OF THE INVENTION

A method and an apparatus for the sampling and the continuous monitoring of the flue gases from an industrial furnace is disclosed. The method is particularly adapted to processes with hostile environments, characterized by high particulate levels and high temperatures and/or vibrations, such as electric arc furnaces (EAF). The method is also adaptable to any industrial combustion processes where flue gas monitoring is desired. Exhaust gases of a furnace are sampled through an extractive probe and analyzed through a remote optical device, preferably a diode laser, for measurement of flue gas species concentration. Thus, an extractive sampling system is integrated with a non-intrusive optical measurement technique that is resistant to the problems encountered by prior art flue gas monitoring systems.

Thus, extractive sampling techniques coupled with gas analyzing systems and in situ optical measurement techniques are combined. Thus, to at least partially overcome the disadvantages of prior art devices, the first preferred embodiment provides a method for effective and near real-time monitoring of furnace flue gases which includes, successively: (1) a system for sampling waste gas flowing along a furnace waste gas duct, such as a gas sampling tube or probe; (2) a drop tube, to conduct the sampled gas from the probe to the remotely positioned measurement device; (3) a drop box, located at the end of this drop tube, upstream the measurement device, so as to remove a large portion of the particulates; (4) an in situ optical device, allowing real-time measurement of the targeted flue gas species concentration (including $O_2$, CO, $CO_2$, $H_2O$, as well as $H_2$ by an indirect means); (5) a particle filter, a condenser and a suction pump for vacuum drawing the gas along the sampling line; and (6) conduit means for venting the measured gas directly into the exhaust duct.

Thus, an object of the present invention is to provide a method for sampling and continuously monitoring flue gases from an industrial furnace that has a more immediate response time and thereby indicates process conditions more quickly, to enable optimal process control.

A further object of the present invention is to provide a method for monitoring the flue gases of an industrial combustion process that provides point measurements, allowing sampling the flue gas specifically in the desired locations of the exhaust stream.

Still another object of the present invention is to provide a method for monitoring the flue gases of an industrial combustion process that facilitates optimal use of the potential energy present in the process by-products, for heat generation.

Yet another object of the present invention is to provide a method for monitoring the flue gases of an industrial combustion process that is not susceptible to probe plugging and corrosion.

An even further object of the present invention is to provide a method for monitoring the flue gases of an industrial combustion process that does not require undue replacement of the monitoring equipment.

Yet another object of the present invention is to provide a method for monitoring the flue gases of an industrial combustion process that provides continuous, near real-time measurements of the species concentration in the waste gases, with acceptable accuracy, so as to facilitate an adapted dynamic monitoring of process characteristics.

An even further object of the present invention is to provide a method for monitoring the flue gases of an industrial combustion process that facilitates better control of the CO and $H_2$ combustion by-products.

Still a further object of the present invention is to provide a method for monitoring the flue gases of an industrial combustion process that monitors most or all species whose concentration can be measured by absorption techniques, e.g., $H_2$, CO, $O_2$, $H_2O$, $CO_2$, $NO_x$ and/or $SO_x$.

Yet another object of the present invention is to provide a method for monitoring the flue gases of an industrial combustion process that can be used in industrial processes that experiences high particle densities, temperature gradients, mechanical vibration, rapid variations in temperature and gas composition, and high radiation loads from the process itself.

Still another object of the present invention is to provide a method for monitoring the flue gases of an industrial combustion process that utilizes a simply constructed, inexpensive and reliable sampling apparatus.

These and other objects, advantages and features of the present invention will be apparent from the detailed description that follows.

BRIEF DESCRIPTION OF THE DRAWINGS

In the detailed description that follows, reference will be made to the following figures.

DETAILED DESCRIPTION OF PREFERRED EMBODIMENTS

Although the preferred embodiments of this invention will be described with reference to the electric arc furnace, it is understood that these embodiments are adaptable in broader contexts. The embodiments are generally adaptable to analysis of flue gas streams, and to the control of industrial combustion processes, in which an optical line-of-sight cannot be made readily available for laser beam transmission in situ of the exhaust stream. Therefore, in addition to electric arc furnaces, other examples include basic oxygen furnaces, reheat furnaces, glass furnaces and other industrial combustion processes characterized by harsh environments and/or high particulate densities.

Generally, as described above, it is desirable to obtain near real-time measurements of the species concentration in the waste gases, with acceptable accuracy, to facilitate an adapted dynamic monitoring of process characteristics and optimal process operation. Better control of the CO and $H_2$ downstream from the combustion would permit a significant increase in furnace efficiency.

In a first preferred embodiment, extractive sampling techniques coupled with gas analyzing systems and in situ optical measurement techniques are combined. Thus, to at least partially overcome the disadvantages of prior art devices, the first preferred embodiment provides a method for effective and near real-time monitoring of furnace flue gases which includes, successively: (1) a system for sampling waste gas flowing along a furnace waste gas duct, such as a gas sampling tube or probe; (2) a drop tube, to conduct the sampled gas from the probe to the remotely positioned measurement device; (3) a drop box, located at the end of this drop tube, upstream the measurement device, so as to remove a large portion of the particulates; (4) an in situ optical device, allowing real-time measurement of the targeted flue gas species concentration (including $O_2$, CO, $CO_2$, $H_2O$, as well as $H_2$, by an indirect means); (5) a particle filter, a condenser and a suction pump for vacuum drawing the gas along the sampling line; and (6) conduit means for venting the measured gas directly into the exhaust duct.

Figure 1:
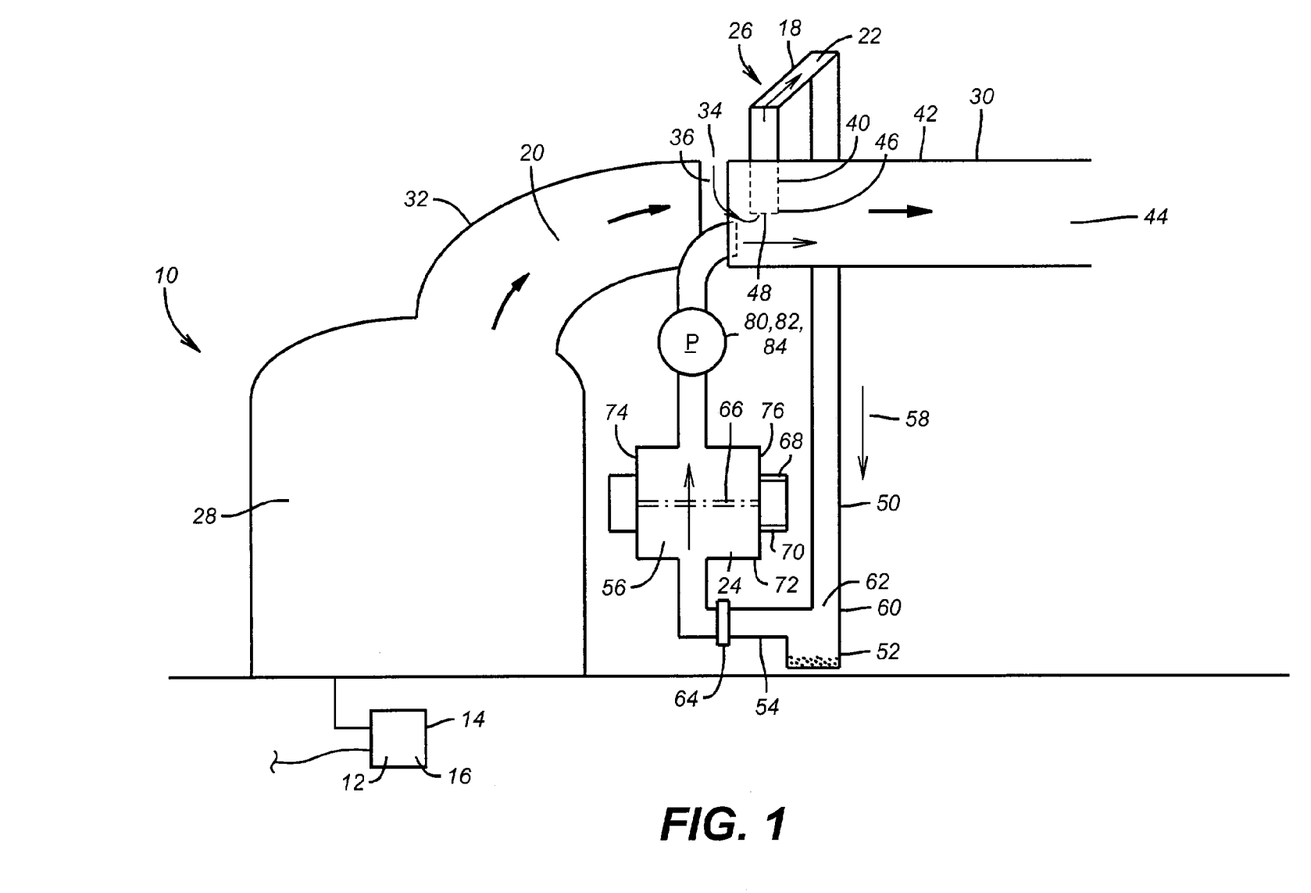
FIG. 1 illustrates a schematic view of a preferred embodiment of a sampling and measuring apparatus.

Looking now at FIG. 1, an apparatus 10 for monitoring off-gas from an electric arc furnace is shown. The electronics 12 of the optical device 14 and the furnace controlling central processing unit 16 are not shown in detail, although these devices process the collected data and control the operation of the process overall. Features of a specific optical scanning system adapted for use with a combustion process can be found in co-pending non-provisional patent application filed 9 Dec. 2002, bearing Ser. No. [to be inserted when received], entitled "Method for Monitoring and Controlling the High Temperature Reducing Combustion Atmosphere," which in turn claims priority to U.S. Provisional Application No. 60/349,638, filed 17 Jan. 2002, entitled "Method for Monitoring and Controlling the High Temperature Reducing Combustion Atmosphere." Both of these applications are expressly incorporated herein by reference.

A small by-pass 18 of the furnace off-gas stream 20 permits redirection of a sample of the process gas 22 to a remote location 24 where it can be measured in near real-time by a non-intrusive optical device 14. As further seen in FIG. 1, measurement of the off-gas 20 is carried out on a sample 22 of waste gas drawn from a process position 26 as close to the furnace 28 as practical, usually at the point where fixed ducting for drawing waste gas from the furnace abuts the movable roof located at the fourth hole elbow of the furnace (details not shown). Note that, in an application where the gas to be sampled is taken directly from the furnace, it is referred to as a flue gas. In the application described, where the waste from an electric arc furnace is withdrawn from the exhaust duct, the sample is referred to as an off-gas.

Thus, the exhaust duct 30 is separated from the furnace elbow 32 by a gap 34 approximately two to eight inches wide. This gap 34 permits air 36 to be drawn into the duct 30, thus mixing with the exhaust stream 20 to facilitate off-gas flowing and cooling. At the same time, this air 30 is not only mixing, but also reacting with CO and $H_2$, thus modifying the initial composition of the off-gases. This phenomenon tends to occur primarily on the peripheral edges of the off-gas stream 20, adjacent the sides of the exhaust duct 30, similar to a boundary layer effect.

The first preferred embodiment thus described provides for point measurements of the off-gas. To obtain a representative sample of off-gas, the sample 22 is drawn approximately from the center portion of the furnace off-stream gas 20. The sample 22 is generally obtained by means of an elongate probe 40, which is preferably inserted vertically downward from the top 42 of the duct 30 or horizontally sideward from the side 44 of the duct 30, so that its inlet end 46 is located in the above-described position.

Several sampling probes are currently available commercially, offering different designs and different standards of performance. The reliability of such sampling devices depends largely on their mechanical resistance (waste gas temperature at this position can reach 1600° C. in a typical EAF) as well as the resistance to plugging due to the dusts which are present in the fumes drawn in the sampling tube. Conventionally, these devices are often designed to withstand high ambient temperatures, by including water cooling systems, and they may incorporate a filter for sieving out dust and other particulate matter entrained in the sampled gas. This is necessary in conventional sampling and analyzing apparatus, in which the entrained particulate matter is drawn through the gas lines and into the gas analyzer, and the dust and particles may clog or even damage the analyzer equipment. Such a system requires a strict maintenance program for optimal performance.

In the first preferred embodiment, the sampled gas 22 is conducted to a remote position 24 for optical measurement and not led to a gas analyzer. This non-intrusive method does require that the gas be conditioned before measurement, that is to say cleaned and cooled, in contrast to a conventional gas analyzer. Additionally, the sampling probe 40 of the first preferred embodiment does not require a particle filter. The absence of filter means in the proposed sampling probe significantly reduces the usual plugging issues associated with such devices.

The first preferred embodiment of the probe 40 permits minimal inclusion of entrained particle matter, as the preferably vertical positioning of the probe 40 in the duct 30, combined with the location of the fume inlet opening 48 to the leeward side of the probe 40, facilitates particulate removal. Consequently, the use of a filter-free probe is enabled.

After being drawn into the sampling probe 40, the sample 22 is sent through a drop tube 50 to a drop box 52 located at ground level. The temperature of the waste gas 20 should be maintained above its dew point to avoid condensation. Condensation of the waste gas 20 in the portions of the sampling system upstream the optical system 14 is undesirable, since molten droplets may solidify and agglomerate on the sampling line walls. To prevent this condensation, a sample tube 54, which conducts the waste gas sample 22 from the probe 40 to a cavity or measurement chamber 56 where it is optically measured, is heated. Alternatively, the sample tube 54 can be thermally insulated. In any case, the gas temperature should be maintained above its dew point along the length of the sampling circuit 58.

Once at the bottom 60 of the drop tube 58, the sampled gas 22 is directed through a 90° elbow 62 towards the optical device 14. The drop box 52 in the sample circuit 58 is positioned at the location of the elbow 62 so that gravity will cause the heaviest particles drawn into the sampling probe 40 to fall into the drop box 52.

Figure 2:
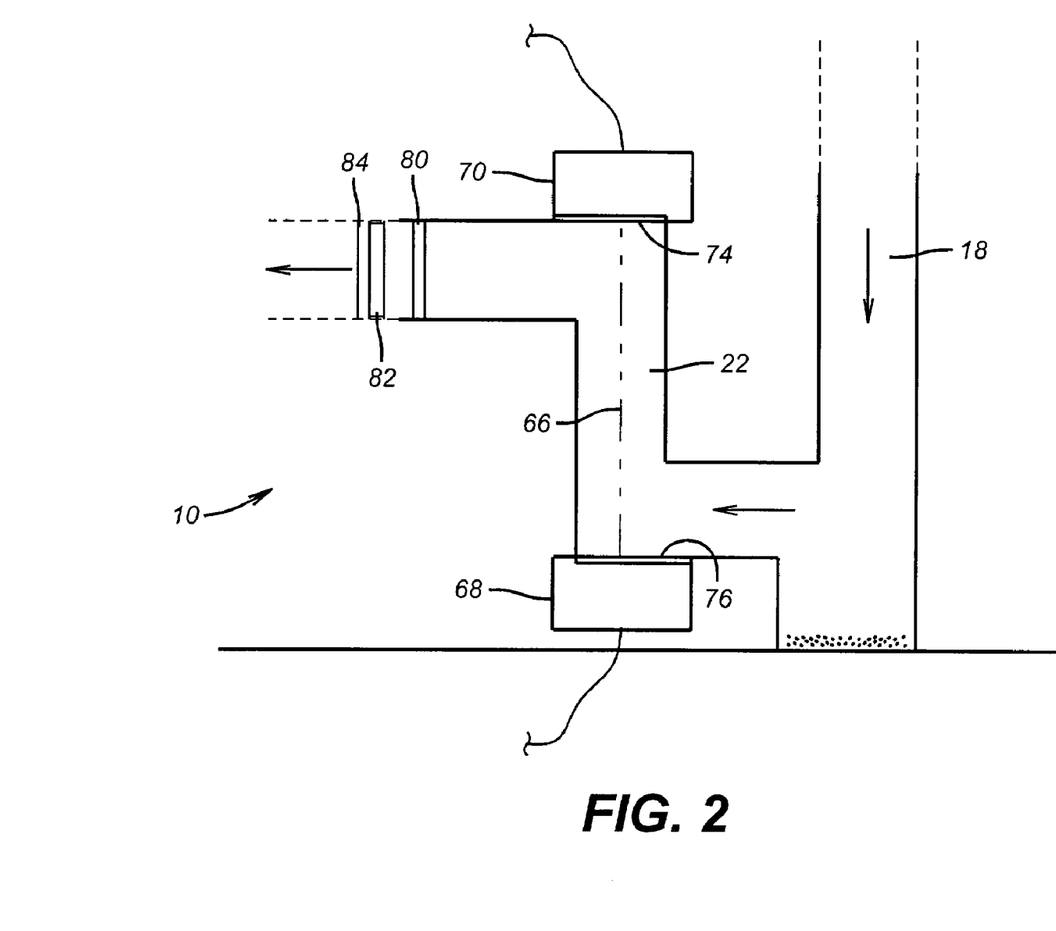
FIG. 2 illustrates a schematic view of another preferred embodiment of a sampling and measuring apparatus.

In a second preferred embodiment, a small-scale electrostatic precipitator 64 removes additional particles from the sample 22, removing up to about 95% of the particles. To use a precipitator 64, the gas streams 22 must be cooled to between about 150° F. and 400° F. This can be accomplished by mixing the drawn gas sample 22 with a stream of cold gas which is not part of the process gas composition, such as nitrogen. Alternatively, the sample stream can be cooled.

The sampled gas is then directed to a cavity or measurement chamber 56 where the concentrations of the off-gas species are measured with a non-intrusive optical system 14. A preferred and more adapted system to carry out such measurements is a tunable diode laser, but this invention can also be adapted for using in situ dispersive, Fourier transform infrared (FTIR) and non-dispersive infrared (NDIR) spectrometry. The preferred approach is using a diode laser for its specificity, sensitivity and dynamic range under conditions experiencing large changes in temperature and concentration.

As schematically shown in FIG. 1, this measurement is accomplished by transmitting a laser beam 66 through the off-gas sample 22 and detecting the beam 66 with an infrared optical detector module 68. An optical signal is then processed by observing the amount of attenuation obtained from the initial beam as the laser is tuned over a resonance absorption line of a given species, so as to obtain the concentration of this species. Finally, an electrical signal based on the species number density is produced, for use in controlling some process variables (furnace pressure, flow rates, etc.) and adjusting the process operation.

Thus, it is possible to monitor all the species whose concentration can be measured by such absorption techniques (tunable diode laser, FTIR, NDIR). The preferred species to be monitored include CO, $O_2$, $H_2O$ and $CO_2$, but additional combustion species such as pollutants ($NO_x$ or $SO_x$) can also be monitored if a full characterization of the off-gas is to be provided. In addition, $H_2$, which has no infrared absorption transitions in high temperature (greater than about 1000° C.) gas streams, can be monitored through an indirect means. One possible method is to introduce $O_2$ downstream of the optical measurement location, which will react with unburned $H_2$ and/or hydrocarbons that may be present, thereby forming $H_2O$ as a product. Then the difference between the measured $H_2O$ downstream and upstream of the $O_2$ injection can be used to back calculate the amount of $H_2$ and/or unburned hydrocarbons in the process stream, through a conventional mass balance.

The embodiment thus described provides fast-time response, due to (a) the optical analysis and (b) the sample lines arrangement that keeps the drop tube length between fifteen and twenty-five feet. In contrast to prior sampling methods, where measurement delays can reach tens of seconds, the first preferred embodiment provides near real-time data about off-gas characteristics having delays of less than about five seconds.

Another advantage of the embodiments thus disclosed is that the measuring environment is more adapted to the use of a laser-based optical sensor. The embodiments provide for minimal degradation of data from particles, beam steering or mechanical vibrations on the laser measurements. As shown, the apparatus 10 provides the transmitter module (launch) 68 and the detector module (receiver) 70 on the same rigid support 72. Mechanical vibrations induced by the furnace 28 are therefore less disruptive to the data, since the launch 68 and the receiver 70 vibrate at about the same frequencies and amplitudes, thus significantly reducing misalignment and noise on the signal. In addition, the close spacing between the launch 68 and receiver 70 reduces the influence of vibrations on the temporal location of the beam 66. Preferably, the transmitter module 68 and the detector module 70 are positioned between about one foot and about five feet apart, with a more preferred range being between about one foot and about three feet, and a most preferred range being between about one foot and about two feet.

Moreover, the two-level particle removal system (adapted probe design and drop box or electrostatic precipitator) of the first preferred embodiment significantly reduces the level of particulate matter present in the measured off-gas, thus minimizing the problem of laser beam attenuation and baseline noise caused by particles flowing through the measured gas volume. This overcomes problems existing traditional in situ optical systems. In such systems, the intensity of the beam transmitted through the off-gas, in the furnace gap, is usually extremely small and difficult to detect in the presence of the large amount of dust and infrared emission from hot particles and gases. Even if signal detection can be enhanced in those cases, through signal processing methods (e.g. wavelength modulation/demodulation technique), it alters the shape of the individual absorption line profiles and then complicates interpretation of experimental measurements. More particularly, measurement of $O_2$ concentrations is often affected by this problem of signal attenuation, because of the short wavelength required. The first preferred embodiment thereby permits and enhances $O_2$ measurements.

The short path length created by the first preferred embodiment further diminishes beam attenuation and beam steering. The path length should be selected according to the species detection requirements (i.e. according to the lowest concentration level to be monitored).

Two opposite windows 74, 76 are provided in the walls 78 of the cavity or measurement chamber 56 where the optical measurement is carried out. These windows 74, 76 are used to transmit the laser beam 66 from the source into the cavity or measurement chamber 56 and then into the detector module 70. Windows 74, 76 are anti-reflection coated to prevent the formation of interference fringes in the detected signal. Their inner surface is purged with a dry gas. This purge, which must be carried out with a gas that is not part of the off-gas composition, prevents the accumulation of dust particles on the surface of the windows 74, 76 and cools the windows (anti-reflection coated windows have a T limit of about 500° C.).

As shown in FIG. 2, a second preferred embodiment 10 includes a laser beam 66 transmitted through the sampled off-gas 22 in the same direction as the gas flow. The path length choice is more flexible, since it is not dependent of the flow section. Following the optical measurement, the sampled off-gas 22 is sent successively through a particle filter 80, a condensing device 82 and a vacuum pump 84 (the combination of these three devices being shown schematically in FIG. 1 by the letter P). This permits the gas to be drawn into the by-pass 18 before being vented back into the furnace exhaust duct 30.

Figure 3:
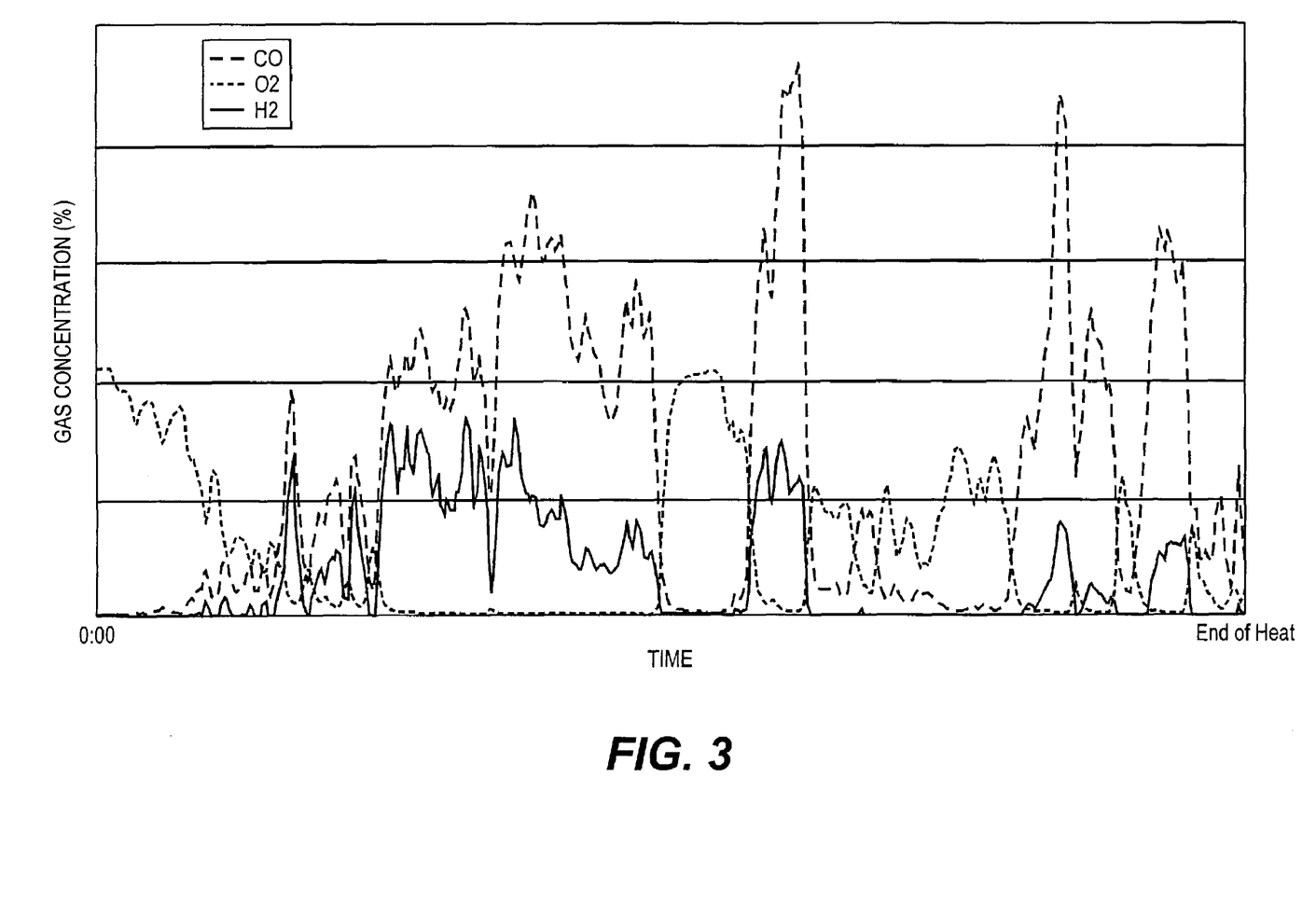
FIG. 3 illustrates expected $O_2$, CO and $H_2$ concentrations in off-gas during a typical EAF heat.

FIG. 3 shows the evolution of $O_2$, CO and $H_2$ concentrations in the course of a typical heat of an electric arc furnace. The CO and $H_2$ concentrations in the furnace off-gas is dependent upon $O_2$ concentration in this same off-gas, such that peak CO and $H_2$ concentrations correspond with $O_2$ concentrations near zero, and vice versa. Consequently, only $O_2$ concentration need be monitored to predict the CO and $H_2$ concentrations. The off-gas monitoring system can also facilitate measuring oxygen concentration in the flue gas and provides post-combustion optimization particularly adapted to electric arc furnaces.

Connecting the off-gas monitoring unit to a process control system, and more preferably to an advanced regulatory system, permits controlling in near real-time the oxygen level in the exhaust gas at a desired set point (e.g. 2%) and changing the oxygen supply to the EAF post-combustion system accordingly. This way, an almost complete burn out of CO, $H_2$ and unburned hydrocarbons is achieved, thus providing minimal off-gas loss and maximum furnace efficiency.

Thus, a system for monitoring the off-gases of an electric arc furnace is disclosed. The system has an exhaust duct separation gap positioned between the furnace exhaust duct and a furnace elbow. The gap has a width of between about two inches and eight inches wide and is constructed and arranged to permit air to be drawn into the duct and mixing with the off-gas. A by-pass circuit communicates a sample of off-gases to be monitored from a furnace or from the furnace exhaust duct, through a measurement chamber and through a return duct being positioned between the measurement chamber and the position from which the sample was drawn, and is thereby constructed and arranged to facilitate return of the sample.

The by-pass circuit further has (a) a gas sampling probe having a fume inlet opening, the probe being positioned for withdrawing a sample of off-gases to be monitored; (b) a drop tube positioned between the gas sampling probe and a drop box, the drop tube having a length of less than about twenty-five feet; (c) a sample tube positioned to conduct the off-gas sample from the probe to a cavity or measurement chamber where it is optically measured; and (d) a drop box located at the end of the drop tube and positioned upstream from a remotely positioned measurement device. The drop box is constructed and arranged to remove particulates that may be present in the off-gases.

An electrostatic precipitator is positioned upstream from the measurement device and constructed and arranged to remove particles from the off-gas sample. Means for cooling the off-gas sample to a temperature of less than about 750 degrees F. is provided to protect the precipitator. A particulate reducing subassembly positioned including a particle filter, a condenser and a suction pump for vacuum drawing the gas along the sampling line is provided.

The remotely positioned measurement device includes a tunable diode laser optical device constructed and arranged to facilitate real-time measurement of targeted off-gas species concentrations for targeted species including at least one of $O_2$, CO, $CO_2$, $H_2O$, and $H_2$. The measurement device further has a transmitter module positioned at a launch position, constructed and arranged to launch a collimated beam of radiation along a line-of-sight path through the off-gas sample, a detector module positioned substantially opposed from the launch position, constructed and arranged to detect the beam, and an optical signal processor. The signal processor is constructed and arranged to (a) detect the attenuation obtained from the initial beam as the laser is tuned over a resonance absorption line of the targeted species, (b) determine the concentration of the targeted species; and (c) report the concentration of the targeted species to a controller constructed and arranged to control at least one process variable in relation to the concentration of the targeted species to optimize the process. Conduit means for venting the measured gas directly into the exhaust duct is provided to complete the by-pass circuit.

A method for monitoring the off-gases of a furnace combustion process is also disclosed. A sample of off-gas to be monitored is routed from a furnace exhaust duct, through a measurement chamber and back to the furnace exhaust duct. A collimated beam of radiation is launched along a line-of-sight path through the off-gas sample. The beam is detected, and the attenuation obtained from the beam as the laser is tuned over a resonance absorption line of the targeted species is detected. The concentration of a targeted species is then determined, and the concentration of the targeted species is reported to a combustion process controller constructed and arranged to control at least one process variable in relation to the concentration of the targeted species to optimize the process. In an embodiment where the targeted species is $O_2$, the process variable includes controlling the $O_2$ level in the furnace to a desired set point and controlling the injection of oxidant into the furnace, thus controlling optimal burn out of CO, $H_2$ and unburned hydrocarbons.

Thus, the preferred embodiments combine advantages of conventional extractive techniques (coupled with gas analysis) and in situ optical techniques (carried out through the exhaust duct). Due to the fast-time response of the optical device, the off-gas monitoring is achieved at near real-time. The accuracy of the results achieved by the optical technique is increased due to the combined reduction of mechanical vibrations and particulate level entrained in the flow. $O_2$ concentration in the flue gas can be measured more precisely, thereby providing improvements in efficiency.

Gas composition measurements are more representative of the process gases because samples can be extracted from ideal locations within the off-gas duct. These three aspects: real-time, accuracy and the measurement of representative samples contribute to the improved process control.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. An apparatus for monitoring the flue gases of a furnace combustion process comprising, in combination:
    a by-pass circuit constructed and arranged to communicate a sample of flue gases to be monitored through a measurement chamber and through a return duct;
    the by-pass circuit having a gas sampling probe having a fume inlet opening, the probe being positioned for withdrawing the sample to be monitored and transmitting it through the by-pass circuit;
    a measurement device positioned in the measurement chamber and comprising an in situ optical device constructed and arranged to facilitate real-time measurement of targeted flue gas species concentrations, the targeted species including at least one of $O_2$, CO, $CO_2$, $H_2O$, and $H_2$, the measurement device further comprising an optical signal processor constructed and arranged to report a measured concentration to a controller that is constructed and arranged to control a process variable in relation to the measured concentration to optimize the process; and
    a vacuum drawing system constructed and arranged to draw the furnace flue gas to be monitored through the by-pass circuit.

2. The apparatus of claim 1, the by-pass circuit further comprising:
    a drop tube in communication with the probe and upstream a drop box; and
    the drop box being located at the end of the drop tube and positioned upstream from the measurement chamber, the drop box being constructed and arranged to remove particulates that may be present in the flue gases.

3. The apparatus of claim 1, wherein the vacuum drawing system comprises a particulate reducing subassembly operatively positioned in the return duct and including a particle filter, a condenser and a suction pump for vacuum drawing the flue gases through the by-pass circuit.

4. The apparatus of claim 1, wherein the probe is a filter-free probe.

5. The apparatus of claim 1, wherein the probe is positioned in the furnace.

6. The apparatus of claim 1, wherein the probe is positioned in the furnace exhaust duct.

7. The apparatus of claim 1, wherein the by-pass circuit is thermally insulated to prevent the flue gas from cooling to a temperature below its dew point along the length of the by-pass circuit.

8. The apparatus of claim 1, further comprising:
    an electrostatic precipitator constructed and arranged to remove particles from the flue gas sample, the precipitator being positioned upstream from the measurement chamber.

9. The apparatus of claim 8, further comprising:
    means for cooling the flue gas sample to a temperature of less than about 750 degrees F.

10. The apparatus of claim 9, wherein the means for cooling the flue gas sample to a temperature of less than about 750 degrees F. comprises:
    mixing the drawn flue gas sample with a stream of neutral, cooler gas which is not part of the process gas composition.

11. The apparatus of claim 10, wherein the neutral, cooler gas is nitrogen.

12. The apparatus of claim 1, wherein the measurement device uses an absorption-based technique to measure the flue gas sample.

13. The apparatus of claim 12, wherein the measurement device is a tunable diode laser.

14. The apparatus of claim 12, wherein the measurement device performs in situ dispersive, Fourier transform infrared (FTIR) spectrometry.

15. The apparatus of claim 12, wherein the measurement device performs non-dispersive, infrared (NDIR) spectrometry.

16. The apparatus of claim 1, the measurement device comprising:
    a transmitter module positioned at a launch position, constructed and arranged to launch a collimated beam of radiation along a line-of-sight path through the flue gas sample;
    a detector module positioned substantially opposed from the launch position, constructed and arranged to detect the beam; and
    an optical signal processor is further constructed and arranged to detect the attenuation obtained from the initial beam as the laser is tuned over a resonance absorption line of the targeted species.

17. The apparatus of claim 16, wherein the transmitter module and the detector module are both mounted on a rigid support.

18. The apparatus of claim 16, wherein the distance between the transmitter module and the detector module is between about one foot and about three feet.

19. An apparatus for monitoring the flue gases of a furnace combustion process comprising, in combination:
    a by-pass circuit constructed and arranged to communicate a sample of flue gases to be monitored through a measurement chamber and through a return duct positioned downstream from the measurement chamber, the by-pass circuit further having
  (a) a gas sampling probe having a fume inlet opening, the probe being positioned for withdrawing a sample of flue gases to be monitored;
  (b) a drop tube positioned between the gas sampling probe and a drop box, the drop tube having a length of less than about twenty-five feet; and
  (c) a drop box located at the end of the drop tube and positioned upstream from a remotely positioned measurement device, the drop box being constructed and arranged to remove particulates that may be present in the flue gases;
an electrostatic precipitator positioned upstream from the measurement device and constructed and arranged to remove particles from the flue gas sample;
means for cooling the flue gas sample to a temperature of less than about 750 degrees F.;
a vacuum drawing system having a particle filter, a condenser and a suction pump for vacuum drawing the gas along the by-pass circuit;
the remotely positioned measurement device comprising a tunable diode laser optical device constructed and arranged to facilitate real-time measurement of targeted flue gas species concentrations, the measurement device further comprising an optical signal processor constructed and arranged to report a measured concentration to a controller that is constructed and arranged to control a process variable in relation to the measured concentration to optimize the process; and
the targeted species including at least one of $O_2$, $CO$, $CO_2$, $H_2O$, and $H_2$; and conduit means for venting the measured gas.

20. The apparatus of claim 19, wherein the probe is a filter-free probe.

21. The apparatus of claim 19, wherein the by-pass circuit is insulated sufficiently to prevent the flue gas from cooling to a temperature below its dew point along the length of the by-pass circuit.

22. The apparatus of claim 19, wherein the means for cooling the flue gas sample to a temperature of less than about 750 degrees F. comprises mixing the drawn flue gas sample with a stream of neutral, cooler gas which is not part of the process gas composition.

23. The apparatus of claim 22, wherein the neutral, cooler gas is nitrogen.

24. The apparatus of claim 19, wherein the fume inlet is positioned on a leeward side of the probe downstream with respect to flow of flue gases past the probe.

25. The apparatus of claim 19, wherein the remotely positioned measurement device comprises:
  a transmitter module positioned at a launch position, constructed and arranged to launch a collimated beam of radiation along a line-of-sight path through the flue gas sample;
  a detector module positioned substantially opposed from the launch position, constructed and arranged to detect the beam; and
  an optical signal processor constructed and arranged to detect the attenuation obtained from the initial beam as the laser is tuned over a resonance absorption line of the targeted species.

26. The apparatus of claim 25, wherein the transmitter and the detector module are both mounted on a rigid support.

27. The apparatus of claim 25, wherein the beam is transmitted in a direction that is substantially, perpendicular to a direction of gas sample flow.

28. The apparatus of claim 25, wherein the beam is transmitted in a direction that is substantially parallel to a direction of gas sample flow.

29. The apparatus of claim 25, wherein the probe is positioned in the furnace.

30. The apparatus of claim 25, wherein the probe is positioned in a furnace exhaust duct.

31. The apparatus of claim 25, wherein the process is electric arc furnace operation, and wherein the probe is positioned proximate to a separation gap positioned between a furnace elbow and a furnace exhaust duct.

32. A system for monitoring the off-gases of an electric arc furnace comprising, in combination:
  a by-pass circuit constructed and arranged to communicate a sample of off-gases to be monitored from a furnace exhaust duct, through a measurement chamber and through a return duct being positioned between the measurement chamber and the furnace exhaust duct, thereby being constructed and arranged to facilitate return of the sample to the furnace exhaust duct;
  the by-pass circuit further having
    (a) a gas sampling, filter-free probe having a fume inlet opening, the probe being positioned proximate to a separation gap in the furnace exhaust duct for withdrawing a sample of off-gases to be monitored;
    (b) a drop tube positioned between the gas sampling probe and drop box, the drop tube having a length of less than about twenty-five feet; and
    (c) a drop box located at the end of the drop tube and positioned upstream from the measurement device, the drop box being constructed and arranged to remove particulates that may be present in the off-gases;
  an electrostatic precipitator positioned upstream from the measurement device and constructed and arranged to remove particles from the off-gas sample;
  means for cooling the off-gas sample to a temperature of less than about 750 degrees F.;
  a vacuum drawing system including a particle filter, a condenser and a suction pump for vacuum drawing the gas along the sampling line;
  the measurement device comprising a tunable diode laser optical device constructed and arranged to facilitate real-time measurement of targeted off-gas species concentrations for targeted species including at least one of $O_2$, $CO$, $CO_2$, $H_2O$, and $H_2$;
  the measurement device further comprising a transmitter module positioned at a launch position, constructed and arranged to launch a collimated beam of radiation along a line-of-sight path through the off-gas sample; a detector module positioned substantially opposed from the launch position, constructed and arranged to detect the beam; and an optical signal processor constructed and arranged to (a) detect the attenuation obtained from the initial beam as the laser is tuned over a resonance absorption line of the targeted species, (b) determine the concentration of the targeted species; and (c) report the concentration of the targeted species to a controller constructed and arranged to control at least one process variable in relation to the concentration of the targeted species to optimize the process; and conduit means for venting the measured gas directly into the exhaust duct.

33. A method for monitoring the flue gases of a furnace combustion process comprising, in combination:
  routing a sample of flue gas to be monitored from a furnace, through a measurement chamber and back to a return duct;

launching a collimated beam of radiation along a line-of-sight path through the flue gas sample;
detecting the beam;
detecting the attenuation obtained from the beam as the laser is tuned over a resonance absorption line of the targeted species;
determining the concentration of a targeted species; and reporting the concentration of the targeted species to a combustion process controller constructed and arranged to control at least one process variable in relation to the concentration of the targeted species to optimize the process.

34. The method of claim 33, wherein the targeted species includes at least one of $O_2$, CO, $CO_2$, $H_2O$, and $H_2$.

35. The method of claim 33, further comprising:
the targeted species being only $O_2$, and the process variable includes controlling the $O_2$ level in the furnace to a desired set point and controlling the injection of oxidant into the furnace, thus controlling optimal burn out of CO, $H_2$ and unburned hydrocarbons.

36. The method of claim 35, wherein the furnace combustion process is operation of an electric arc furnace.

* * * * *